US006676835B2

(12) United States Patent
O'Connor et al.

(10) Patent No.: US 6,676,835 B2
(45) Date of Patent: Jan. 13, 2004

(54) MICROFLUIDIC SEPARATORS (75) Inventors: Stephen D. O'Connor, Pasadena, CA (US); Christoph D. Karp, Pasadena, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/131,969

(22) Filed: Apr. 23, 2002

(65) Prior Publication Data

US 2002/0113009 A1 Aug. 22, 2002

Related U.S. Application Data (62) Division of application No. 09/632,681, filed on Aug. 7, 2000.

(51) Int. Cl.[7] .............................................. B01D 17/00
(52) U.S. Cl. .................. 210/542; 137/833; 204/600; 210/321.84; 210/511; 422/100; 422/101; 428/166; 428/188
(58) Field of Search .................. 210/511, 542, 210/634, 321.68, 321.84; 366/338–340, 336; 422/129, 99, 100, 101; 204/600, 601; 216/2, 56; 209/155; 137/833; 428/137, 166, 188

(56) References Cited

U.S. PATENT DOCUMENTS

| 5,534,328 | A | * | 7/1996 | Ashmead et al. | |
| 5,595,712 | A | * | 1/1997 | Harbster et al. | |
| 5,726,026 | A | | 3/1998 | Wilding et al. | ............. 437/7.21 |
| 5,932,100 | A | | 8/1999 | Yager et al. | ................ 210/634 |
| 5,971,158 | A | | 10/1999 | Yager et al. | ................ 209/155 |
| 6,074,725 | A | * | 6/2000 | Kennedy | ..................... 428/188 |
| 6,136,272 | A | | 10/2000 | Weigl et al. | ............. 422/82.05 |
| 6,190,034 | B1 | | 2/2001 | Nielsen et al. | ............. 366/336 |
| 6,409,072 | B1 | * | 6/2002 | Breuer et al. | |
| 6,494,614 | B1 | * | 12/2002 | Bennett et al. | ............. 366/341 |
| 6,499,499 | B2 | * | 12/2002 | Dantsker et al. | ............ 137/833 |

FOREIGN PATENT DOCUMENTS

| EP | 1 123 734 | 8/2001 | ............ B01J/19/00 |
| WO | WO 99/19717 | 4/1999 | |
| WO | WO 99/60397 | 11/1999 | |

* cited by examiner

*Primary Examiner*—Joseph Drodge
(74) *Attorney, Agent, or Firm*—Vincent K. Gustafson; Michael F. Labbee (57) ABSTRACT

Microfluidic separators for separating multiphase fluids are described. Two or more microfluidic outlet channels within the device meet at an overlap region. The overlap region may be in fluid communication with an inlet channel. The inlet channel and each outlet channel are disposed within different layers of a three-dimensional device. Each channel is defined through the entire thickness of a stencil layer. A multiphase fluid flows through an inlet channel into an overlap region from where the separated phases can be withdrawn through the outlet channels.

23 Claims, 6 Drawing Sheets

MICROFLUIDIC SEPARATORS

STATEMENT OF RELATED APPLICATION(S)

This application is filed as a divisional application of U.S. patent applicton Ser. No. 09/632,681, filed Aug. 7, 2000 and currently pending.

FIELD OF THE INVENTION

The present invention relates to microfluidic devices and the manipulation of fluid flow within those devices. These devices are useful in various biological and chemical systems, as well as in combination with other liquid-distribution devices.

BACKGROUND OF THE INVENTION

There has been a growing interest in the manufacture and use of microfluidic systems for the acquisition of chemical and biological information. In particular, microfluidic systems allow complicated biochemical reactions to be carried out using very small volumes of liquid. These miniaturized systems increase the response time of the reactions, minimize sample volume, and lower reagent cost.

Traditionally, microfluidic systems have been constructed in a planar fashion using silicon fabrication techniques. Representative systems are described, for example, by Manz, et al. (Trends in Anal. Chem. (1990) 10(5): 144–149; Advances in Chromatography (1993) 33: 1–66). These publications describe microfluidic devices constructed using photolithography to define channels on silicon or glass substrates and etching techniques to remove material from the substrate to form the channels. A cover plate is bonded to the top of this device to provide closure.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy, et al., Analytical Chemistry (1998) 70: 4974–4984; McCormick, et al., Analytical Chemistry (1997) 69: 2626–2630), or by building a traditional injection molding cavity for plastic devices. Some molding facilities have developed techniques to construct extremely small molds. Components constructed using a lithography, electroplating and molding (LIGA) technique have been developed (see, e.g., Schomburg, et al., Journal of Micromechanical Microengineering (1994) 4: 186–191). Other approaches combine LIGA and a hot-embossing technique. Imprinting methods in polymethylmethacrylate (PMMA) have also been demonstrated (see, e.g., Martynova, et al., Analytical Chemistry (1997) 69: 4783–4789). However, these techniques do not lend themselves to rapid prototyping and manufacturing flexibility. Additionally, these techniques are limited to planar structures. Moreover, the tool-up costs for both of these techniques are quite high and can be cost-prohibitive.

Generally, the mixing of fluids in a microfluidic system is problematic, since the fluid flow within these devices is not turbulent. Some microfluidic mixing devices have been constructed in substantially planar microfluidic systems where the fluids are allowed to mix through diffusion (see Bokenkamp, et al., Analytical Chemistry (1998) 70(2): 232–236. In these systems, the fluids only mix at the interface of the fluids, which is commonly small relative to the overall volume of the fluids. Thus, very little mixing occurs.

Alternative mixing methods have been developed based on electrokinetic flow. Such devices are complicated, requiring electrical contacts within the system. Additionally such systems only work with charged fluids, or fluids containing electrolytes. Finally, these systems require voltages that are sufficiently large that water is electrolyzed, which means bubble formation is a problem and samples cannot be easily collected without being destroyed.

There is, thus, a need for a robust mixing device capable of thoroughly mixing a wide variety of fluids in a microfluidic environment in a controlled manner at relatively high speed.

SUMMARY OF THE INVENTION

In a first separate aspect of the invention, a microfluidic separator includes an inlet channel defined through the entire thickness of a first stencil layer, a first outlet channel defined through the entire thickness of a second stencil layer, a second outlet channel defined through the entire thickness of a third stencil layer, and an overlap region permitting fluid to be communicated from the inlet channel to both the first outlet channel and the second outlet channel. The first stencil layer is disposed between the second stencil layer and the third stencil layer.

In a second separate aspect of the invention, a microfluidic separator includes an inlet channel defined through the entire thickness of a first device layer, a second device layer disposed above the first device layer and defining a first outlet channel, and a third device layer disposed below the first device layer and defining a second outlet channel. The first device layer terminates in an overlap region, with both the second device layer and the third device layer being in fluid communication with the overlap region.

In another aspect, any of the foregoing aspects may be combined for additional advantage.

These and other aspects and objects of the present invention will become apparent to one skilled in the art upon reviewing the description, drawings, and appended claims.

DETAILED DESCRIPTION OF PREFERRED EMBODIMENTS OF THE INVENTION

Definitions

The term "channel" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" may be filled or may contain internal structures comprising valves or equivalent components.

The term "microfluidic" as used herein is to be understood, without any restriction thereto, to refer to structures or devices through which fluid(s) are capable of being passed or directed, wherein one or more of the dimensions is less than 500 microns.

Preferred Fluidic Devices

Certain embodiments of the present invention are directed to microfluidic mixing devices that provide rapid mixing of two or more fluids and include microfluidic systems capable of mixing various fluids in a controlled manner based on the design and construction of the devices. In one embodiment, these devices contain microfluidic channels that are formed in various layers of a three dimensional structure. The various channels intersect in certain areas in order to produce mixing of the fluids in the various channels. The amount of overlap, geometry of the overlaps, surface chemistry of the overlaps, fluid used and flow rate of the fluids all have a controllable effect on the amount of mixing.

In one embodiment, a microfluidic device according to the present invention has at least two inlet channels on different substantially planar, horizontally disposed, layers of the device. Such layers can be flexible, to permit the overall device to conform to a non-planar shape and remain operable. The layers containing the inlet channels can be adjacent or can be separated by one or more layers. The inlet-channels meet at an overlap region. Where the channel-containing layers are stencil layers, with the channels cut through the layers, the inlet channels must not overlap vertically until the overlap region, unless an intermediate layer is used. An outlet channel may be provided that is in fluid communication with the overlap region, such that fluid flowing through the inlet channels must enter the overlap region and exit through the outlet channel.

The inlet channels are in fluid communication at the overlap region. The overlap region is also in fluid communication with an outlet channel, if an outlet channel is provided. The outlet channel can be on the same layer as one of the inlet channels or can be on a different layer. In a preferred embodiment, the outlet channel is on a layer intermediate between the inlet channels.

This design produces sufficient interface per cross-sectional area between the different fluid streams to effect rapid mixing. In this manner, diffusional mixing is achieved between two or more fluids that meet at the overlap region, and they can mix to a greater degree than is usual in a microfluidic device. The shape and the amount of overlap at those points can be controlled in order to alter the amount of mixing.

In a preferred embodiment, a microfluidic device comprises a plurality of microfluidic inlet channels and an overlap region within which said inlet channels are in fluid communication with each other. In a particular embodiment, at least one inlet channel is formed in a first sheet of a first material and at least another inlet channel is formed in a second sheet of a second material. The materials of the sheets may or may not be the same. For example, one sheet may be made of hydrophobic materials whereas the other sheet may be made of hydrophilic materials. The sheets may be made of materials that expedite fluid flow through the channels. Thus, the material of individual sheets may be selected depending on the composition and chemical nature of the fluid flowing through individual channels.

In another embodiment, a microfluidic device comprises a first inlet channel which is substantially parallel to the top and the bottom surfaces of the first sheet, a second inlet channel which is substantially parallel to the top and the bottom surfaces of the second sheet, and an overlap region within which said first and second inlet channels are in fluid communication with each other. In this embodiment the microfluidic device can further comprise an outlet channel in fluid communication with the inlet channels through the overlap region. In one embodiment, the outlet channel is formed in the first sheet or the second sheet. In a further version of this embodiment the first sheet and the second sheet are joined together such that the plane of the joint is substantially parallel to the top and bottom surfaces of the sheets.

A further embodiment of the invention comprises an outlet channel formed in a third sheet of the material such that the outlet channel is in a plane that is substantially parallel to the top and bottom surfaces of the third sheet. Further, the first, second and third sheets are joined together such that the planes of the joints are substantially parallel to the top and bottom surfaces of the sheets. Alternatively, the third sheet may be joined to both the first sheet and the second sheet.

In another embodiment, a microfluidic mixer comprises a first sheet having a first channel through which a first fluid flows, a second sheet having a second channel through which a second fluid flows, and an overlap region formed by the first and second channels such that the first fluid and the second fluid enter the overlap region and mix therein. This embodiment may further comprise an outlet channel in fluid communication with the inlet channels through the overlap region. Such an outlet channel, for example, is formed in the first sheet or the second sheet. Alternatively, the outlet channel may be formed by in a substantially flat third sheet of the material such that the outlet channel is in a plane that is substantially parallel to the top and bottom surfaces of the third sheet.

In another embodiment, a microfluidic mixer comprises a first channel through which a first fluid flows, a second channel through which a second fluid flows, and an overlap region formed by the first and second channels such that the first fluid and the second fluid enter the overlap region and mix therein to form a mixture of the first and second fluids. Such a mixer may further comprise an outlet channel connected to the overlap region such that the mixture from the overlap region may flows through the outlet channel.

The first and second fluids supplied to a mixer may be substantially the same or may differ in one or more of their properties, such as, viscosities, temperatures, flow rates, compositions.

In another embodiment, a device comprises two or more microfluidic inlet channels that are located within different layers of a three-dimensional device. The inlet channels are designed such that the flows of the fluids overlap, with a membrane separating the fluids from each other, and the flows run substantially in the same direction. The inlet channels end at an overlap region. The combined fluid flow then continues into the outlet channel that begins at the same overlap region. This outlet channel is in a layer between the two inlet channels, and is designed such that the direction of the resulting combined fluid flows in the same direction as the inlet fluids. Alternatively, the outlet channel can simply be an extension of one of the inlet channels.

In certain embodiments, a microfluidic device contains one or more of these fluidic overlaps. In certain embodiments, all of the fluidic mixers are identical. In other embodiments, the mixers differ within a single device in order to produce preferential mixing. In certain embodiments, the mixers are multiplexed within a device to perform various applications. In another embodiment, the mixers are multiplexed within a device to create the possibility for combinatorial synthesis of various types of materials.

Microfluidic devices according to the present invention can also act as phase separators. A microfluidic device may be constructed with one inlet channel. The inlet channel terminates in an overlap region. A channel in the layer above the inlet channel and a channel in the layer below the inlet channel overlap the termination of the inlet channel as described above in the mixer embodiment. In use, a fluid enters the inlet area. Phase separation may occur in the inlet channel so that at the outlet channels two phases are separated into the two outlet channels. Examples of phase separation could be from oil/water mixtures where the oil rises to the top half of the inlet region and the water goes to the bottom portion. The oil then is withdrawn through the top inlet channel and the water exits out the bottom channel, resulting in separated phase streams.

The top portion of the inlet channel can be constructed from a different polymer than the bottom portion so as to expedite the phase separation. For example, in an organic/aqueous phase separation, the top half could be constructed from a hydrophobic material and the bottom half from a hydrophilic material. In use, the fluid within the channel will rearrange with the organic portion in the top half near the hydrophobic region and the aqueous portion in the bottom half near the hydrophilic region. The exit channels can be made of different materials as well to enhance this phase separation.

Thus, in a preferred embodiment, a microfluidic separator comprises a first channel formed by removing a volume of material equal to the volume of the first channel from a substantially flat first sheet of the material such that the channel is substantially parallel to the top and the bottom surfaces of the first sheet, a second channel formed by removing a volume of material equal to the volume of the second channel from a substantially flat second sheet of the material such that the channel is substantially parallel to the top and the bottom surfaces of the second sheet, a third channel formed by removing a volume of material equal to the volume of the third channel from a substantially flat third sheet of the material such that the channel is substantially parallel to the top and the bottom surfaces of the third sheet, and an overlap region within which said first, second and third inlet channels are in fluid communication with each other. In one version of this embodiment, the first sheet is sandwiched between the second and third sheets whereby the second channel is in fluid communication with the top half of the overlap region and the third channel is in fluid communication with the bottom half of the overlap region. In such a device, a fluid comprising a two-phase mixture is fed to the first channel under conditions sufficient to separate the two phases with the separated phases entering the overlap region such that one of the separated phases is withdrawn through the second channel and another of the separated phases is withdrawn through the third channel.

This embodiment may be such that the materials of the first, second and third sheets are substantially the same. Further, the materials of the second and third sheets can be selected such that the separation of the phases is expedited. For example, in one embodiment, the materials of the of the second and third sheets are selected such that the material of one of the sheets is hydrophobic and the material of another of the sheets is hydrophilic.

In another embodiment the above separator can be used in a method for separating phases of a multi-phase mixture. The method comprises the steps of feeding a fluid comprising a multi-phase mixture to the first channel under conditions sufficient to separate the two phases such that the separated phases enter the overlap region, withdrawing one of the separated phases through the second channel, and withdrawing another of the separated phases through the third channel.

In another embodiment, a method for manufacturing a microfluidic mixing device comprises the steps of removing a volume of material equal to the volume of a first channel from a substantially flat sheet of the material such that the channel is substantially parallel to the top and bottom surfaces of the sheet, removing a volume of material equal to the volume of a second channel from a substantially flat sheet of the material such that the channel is substantially parallel to the top and bottom surfaces of the sheet, and forming an overlap region within which said first and second channels are in fluid communication with each other.

In still another embodiment, a method for mixing two or more fluids comprises transporting a first fluid at a first flow rate and a second fluid at a second flow rate through said first and second inlet channels of the various microfluidic devices described above. This method may be implemented under conditions such that the flow rates are substantially the same. Alternatively, the flow rates are controlled to change the composition in the overlap region of the devices described above.

Each of the inlet and outlet channels of the above devices and mixers may be formed, for example, by removing a volume of material equal to the volume of the channel from a substantially flat sheet of the material. Examples of methods for removing the materials are set forth in applications, U.S. patent application Ser. Nos. 09/550,184, now U.S. Pat. No. 6,561,208, and 09/453,029, now abandoned (published PCT application WO 01/25,138), the entire contents of which are herein incorporated by reference.

Examples of microfluidic devices according to the present invention include devices wherein the volume of the inlet channels is between about 1 nanoliter to about 50 microliters per centimeter length of the inlet channel. The inlet channels have a rectangular or a square cross section with the length of each side between about 1 and about 500 microns. Alternatively, the inlet channels have a circular cross section with the diameter of the inlet channels between about 10 microns to about 1000 microns. Generally, channels have at least one dimension less than about 500 microns. Channels also have an aspect ratio that maximizes surface-to-surface contact between fluid streams. A channel of the invention can have a depth from about 1 to about 500 microns, preferably from about 10 to about 100 microns, and a width of about 10 to about 10,000 microns such that the aspect ratio (width/depth) of the channel cross section is at least about 2, preferably at least about 10, at the overlap region where the channels meet. A channel can be molded into a layer, etched into a layer, or can be cut through a layer. Where a channel is cut through a layer, the layer is referred to as a stencil layer.

Importantly, the nature of these microfluidic mixers may be tuned for particular applications. Some of the parameters that affect the design of these systems include the type of fluid to be used, flow rate, and material composition of the devices. The microfluidic mixers described in the present invention can be constructed in a microfluidic device by controlling the geometry and chemistry of junction points.

Figure 3A:
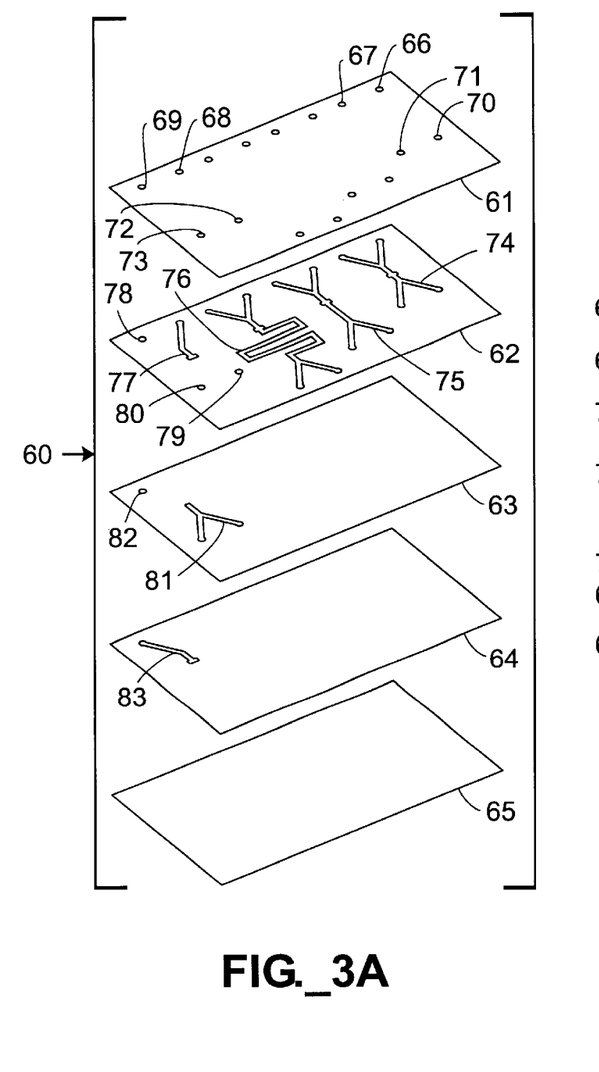
FIG. 3A is an exploded perspective view of a five-layer microfluidic device having four distinct regions each terminated by a splitter: three regions provide ineffective mixers, and the fourth provides a region capable of promoting complete mixing between two fluid streams.
Figure 3B:
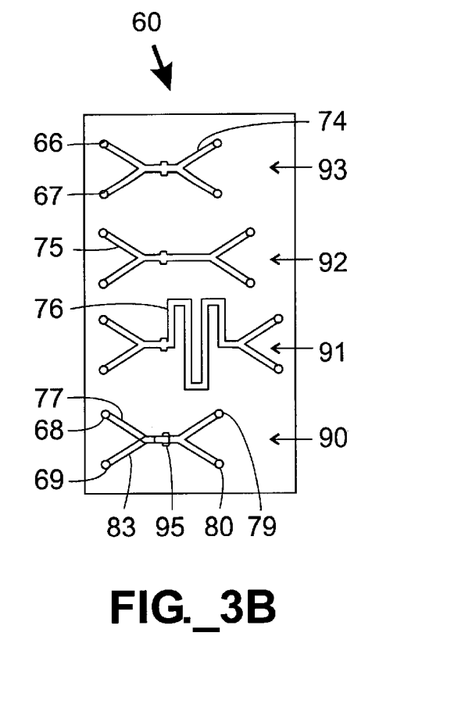
FIG. 3B is a top view of the assembled device of FIG. 3A.

Traditional, less effective microfluidic mixing devices have fluidic channels on a single substantially planar layer of a microfluidic device. Typically, the aspect ratio of these channels is 10:1 or greater. Such a constraint is in part a limitation of the silicon fabrication techniques used to produce such devices. The width of the channels is typically 10 to 500 times greater than the height of the channels. In order to mix samples, two coplanar inlet channels are brought together into a common outlet channel. The fluids meet at the intersection and proceed down the outlet channel. In microfluidic systems, all fluid flow is laminar (no turbulent flow occurs); thus, any mixing in this outlet channel occurs through diffusional mixing at the interface between the inputted liquid streams. This mixing is extremely slow since the interface between the two intersecting fluids is along the smaller dimensions of the perpendicular cross-sections of the fluid streams and is very small compared to the overall volume of the fluids. Since in these traditional microfluidic systems all channels are contained within the same substantially planar layer of the device, this problem is difficult to overcome. Relatively ineffective microfluidic mixers approximating prior art designs but constructed with a stencil fabrication method are shown in FIGS. 3A and 3B.

In devices according to the present invention, fluidic channels are located on different layers of a multi-layer, three-dimensional device. When the channels are brought together to converge into a common channel, the interface between the two fluids is along the horizontal dimension of the channels, which is the larger dimension of the perpendicular cross-section of the fluid streams. The larger interface maximizes the diffusion area between the fluids. In this manner, the majority of the volume of the fluids is in very close proximity to the diffusion interface of the mixing fluids and mixing occurs very rapidly. Importantly, the nature of these overlap regions should be carefully controlled in order to optimize the mixing, as will be described below.

In certain embodiments, the overlap region comprises one or more sheets containing apertures in fluid communication with the inlet channels.

In certain embodiments, the devices may further comprise an upper sheet, wherein the upper sheet defines the top surface of one inlet channel. Further, the devices may comprise a lower sheet, wherein the lower sheet defines the bottom surface of another inlet channel. These upper and lower sheets in certain embodiments are substantially rigid.

Preferable materials for constructing microfluidic devices according to the present invention include paper, foil or plastics. Examples of plastics include those selected from the group consisting of polytetrafluoroethylenes, polycarbonates, polypropylenes, polyimide and polyesters. Thus, the sheets of devices according to the present invention can be made of plastic, paper or foil. The sheets of such devices can be joined together such that the plane of the joint is substantially parallel to the top and bottom surfaces of the sheets. In one embodiment, the first, second and third sheets are joined together such that the planes of the joints are substantially parallel to the top and bottom surfaces of the sheets. In another embodiment, the third sheet is joined to both the first sheet and the second sheet such that it is sandwiched between the first and the second sheet.

In a preferred embodiment, these devices are constructed using stencil layers to define channels and/or chambers. A stencil layer is substantially planar and has at least one channel cut through it, such that in the final device, the top and bottom surfaces of the microfluidic channel are defined by the bottom and top surfaces, respectively, of adjacent stencil or substrate layers. The stencils are preferably sandwiched between substrates, wherein the substrates are preferably substantially planar. Stencil layers are bonded by any technique that results in substantially liquid-tight channels within the device. A stencil can, for example, be self-adhesive to form a seal between adjacent substrates. Alternatively, an adhesive coating can be applied to stencil layers. Alternatively, stencil layers may be held together using gaskets and/or mechanical force. Alternatively, applying heat, light or pressure can activate adhesion. The construction of microfluidic devices from stencil layers and substrates is described in applications, U.S. patent application Ser. Nos. 09/550,184, now U.S. Pat. No. 6,561,208, and 09/453,029, now abandoned (published PCT application WO 01/25,138), the entire contents of which are incorporated herein by reference.

In one embodiment, the stencil layers are comprised of single- or double-sided adhesive tape. A portion of the tape (of the desired shape and dimensions) can be cut and removed to form channels, chambers and apertures. A tape stencil can then be placed on a supporting substrate or between other device layers, including other layers made of tape. In one embodiment, stencil layers can be stacked on each other. In this embodiment, the thickness or height of the channels can be varied by simply varying the thickness of the stencil (e.g., the tape carrier and the adhesive or glue thereon) or by using multiple identical stencil layers stacked on top of one another.

Various types of tape are useful in the above embodiment. Single- or double-sided self-adhesive tape is preferred. The type of glue or adhesive can be varied to accommodate the application, as can the underlying carrier's thickness and composition. Such tapes may have various methods of curing, including pressure-sensitive tapes, temperature-curing tapes, chemically-curing tapes, optical-curing tapes, and other types of curing tapes. Examples include tapes that use rubber-based adhesive, acrylic-based adhesive, and other types of adhesive. The materials used to carry the adhesive are also numerous. Examples of suitable tape carrier materials include polyesters, polycarbonates, polytetrafluoroethylenes, polypropylenes, polyimides (e.g., KAPTON™) and polyesters (e.g., MYLAR™). The thickness of these carriers can be varied.

In yet another embodiment, the layers are not discrete, but a layer describes a substantially planar section through such a device. Such a device can be constructed using photopolymerization techniques such as those described in Cumpston B. H., et al. (1999) Nature 398:51–54.

Example Devices

Figure 1A:
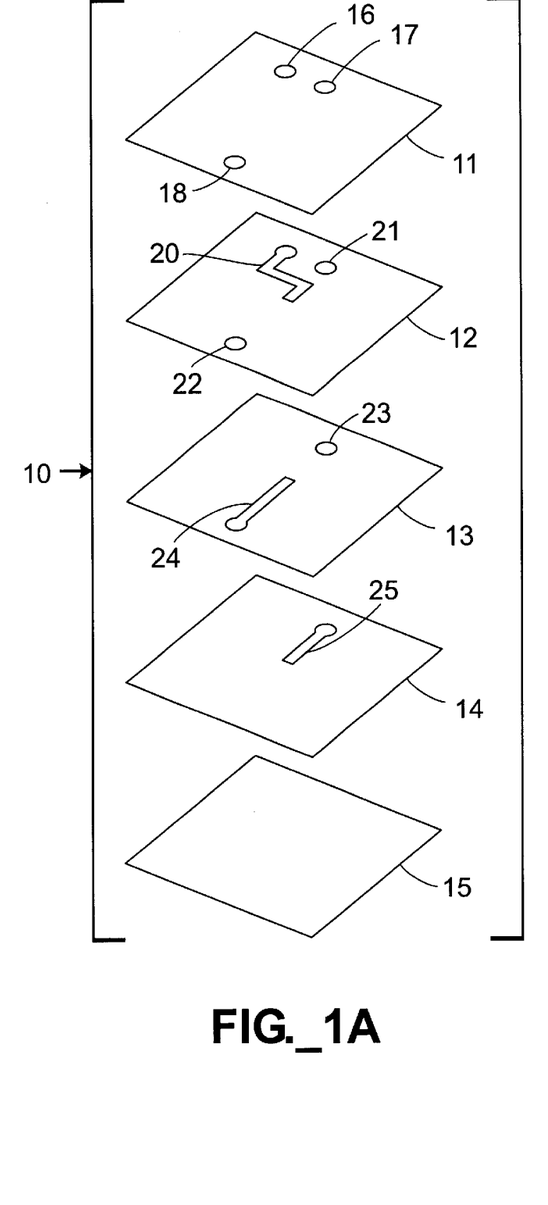
FIG. 1A is an exploded perspective view of a five-layer microfluidic device capable of mixing two fluids.
Figure 1B:
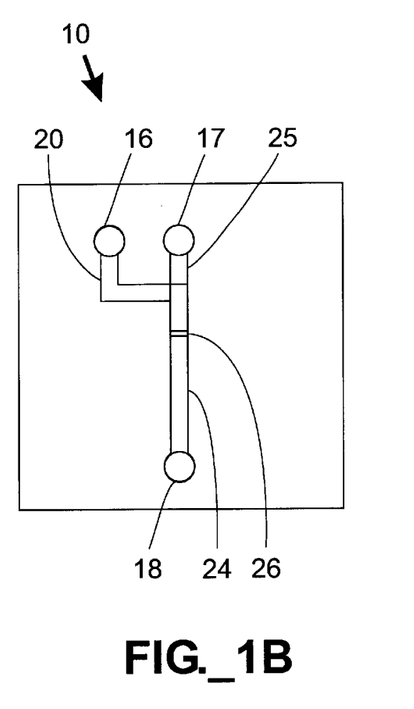
FIG. 1B is a top view of the assembled device of FIG. 1A.

In the embodiment shown in FIGS. 1A–1B, a microfluidic mixing device 10 is constructed with sandwiched stencil layers. Referring to FIG. 1A, a microfluidic mixer 10 is constructed by sandwiching three stencil layers 12–14 and adhering them between substrates 11,15. The stencil layers 12-14 define various channels 20, 24, 25 and apertures 16–18, 21–23. Inlet ports 16,17 and an outlet port 18 are in the top device layer 11. The assembled device 10 is shown in FIG. 1B. In use, a first fluid is injected into inlet port 17, passes through through-holes 21, 23 in the layers 12 and 13 and enters the channel 25. A second fluid enters inlet port 16 and passes through channel 20. The two fluids meet at the overlap region 26 shown in FIG. 1B. At this point, the fluids are forced to converge into a single channel 24 defined in stencil layer 13. As the fluids meet and pass into channel 24, the top half of the channel 24 contains the second fluid and the bottom half contains the first fluid. The heights of these channels 20, 24, 25 are relatively small (between 100 nanometers and 500 microns), so diffusional mixing occurs quickly and a homogenous material is transported off-board at exit port 18. It has been discovered that the majority of the mixing occurs at the junction point 26, with a slight amount of mixing occurring within channel 24 immediately downstream of the junction point 26. The amount of mixing that occurs after the junction point 26 depends on a number of factors, including geometry of the channels, chemical make-up of the channels and samples, flow rate, etc.

In the embodiment shown in FIGS. 1A–1B, the three channels 20, 24, 25 that meet at point 26 are all the same width. Surprisingly, it has been discovered that if the layers containing the channels are not well-aligned, proper mixing does not occur. The fluid entering outlet channel 24 is a mixture of the two input fluids only in mixers where the channels 20, 24 and 25 all overlap. If, for example, inlet channel 20 is misaligned laterally such that for a small portion of the overlap there is an area where only the inlet channel 20 and the outlet channel 24 overlap, then in this region only the fluid from inlet channel 20 will enter outlet channel 24. The remainder of the fluid entering outlet channel 24 will be a mixture of the two input fluids; this will cause a "streaking" effect, where a flow of mixed fluids runs parallel with an unmixed fluid through the outlet channel 24. These "streaking" problems are easily overcome by the following modifications.

Figure 2A:
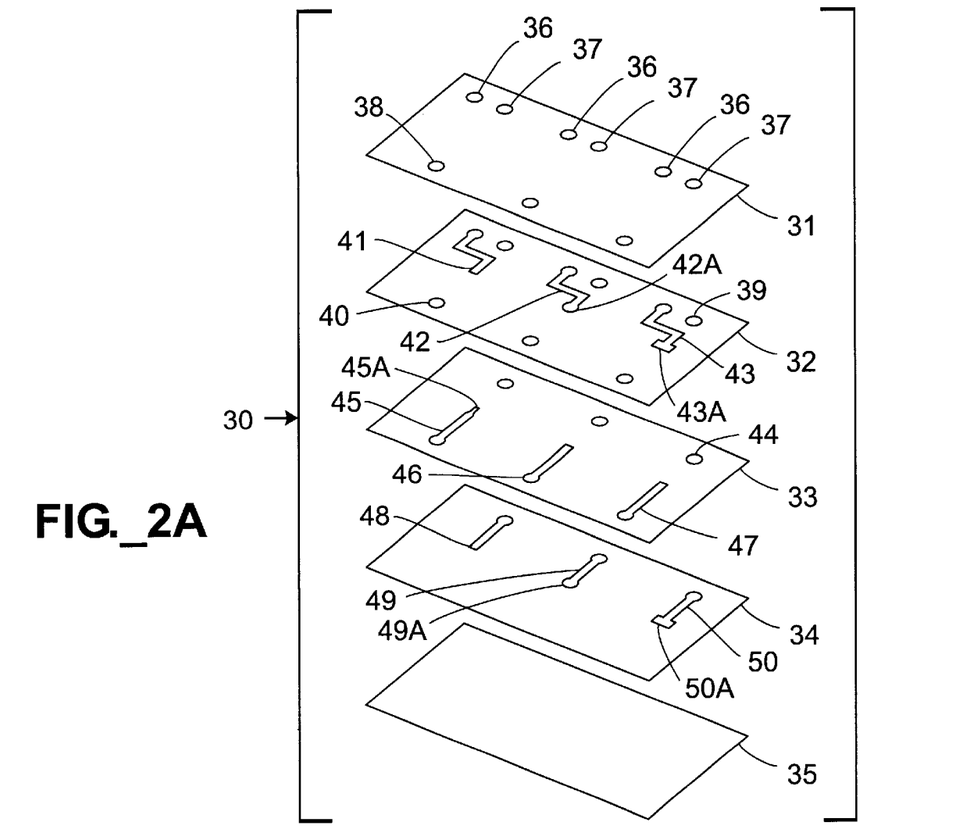
FIG. 2A is an exploded perspective view of a five-layer microfluidic device according to the present invention, the device providing three distinct regions illustrating different channel overlap geometries.
Figure 2B:
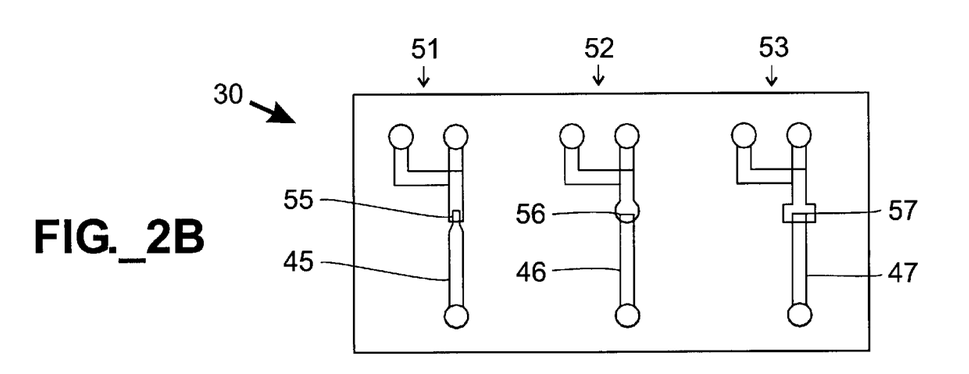
FIG. 2B is a top view of the assembled device of FIG. 2A.

Preferred mixer embodiments are shown in FIGS. 2A–2B. These embodiments do not suffer from the same strict alignment parameters as the mixer 10 shown in FIGS. 1A–1B. Referring to FIG. 2A, three different microfluidic mixers 51–53 are built into a single device 30. The device 30 is constructed from five device layers 31–35 including stencil layers 32–34. Stencil layers 32–34 define channels 41–43, 45–47, 48–50; through holes 39, 40, 44; entry ports 36, 37; and exit ports 38. The stencil layers 32–34 are adhered together between outer device layers 31, 35 to form the completed device 30, shown in FIG. 2B. Notice that the shapes of the overlap regions 55–57 in these mixers 51–53 are shaped so that slight misalignment of device layers during construction will not have a great effect on fluid flow and mixing. It has been found that mixers 51–53 such as in FIGS. 2A–2B are far superior to the mixer 10 shown in FIGS. 1A–1B, for the above-outlined reason.

In another preferred embodiment, changing the chemical nature in the overlap region alters the overlap junction. This can be accomplished by forming the stencil from a different material, or altering the surface chemistry of this stencil layer. The surface chemistry can be altered in many-ways, as one skilled in the art will realize. These methods of altering the surface chemistry include chemical derivatization as well as surface modification techniques such as plasma cleaning or chemical etching. The chemical derivatization is preferably chosen such that fluids flow through the channels and overlap region occurs smoothly and without bubble formation.

The above-described methods for altering the overlap junction within a microfluidic device can be used independently or in conjunction with one another. Other methods for altering the nature of the junction are also included, if not specifically stated.

One surprising aspect of the present invention is that the optimal parameters for a given overlap are greatly affected by the nature of the sample that is to be used within the device. It has been found that the optimal geometry for these overlaps changes depending upon the solution used.

The mixing between two or more fluid channels can be adjusted to give a tremendous range of different ratios. The main or easiest way to do this is to hold the flow rate of one channel constant, while adjusting the flow rate of the other channel. In this way, different mixture ratios are formed by virtue of different quantities of each liquid entering the mixing chamber/overlap area in a given time period. Another method is to alter the size of the channels leading into the mixing region; this has the effect of changing the flow rate internally. This would be useful for arrays, where different ratios are desired without the hassle of using different external flow rates.

The mixing characteristics of a microfluidic mixer according to the present invention were compared to a number of microfluidic mixers according to more conventional designs. Referring to FIGS. 3A–3B, a single device 60 is constructed that contains four independent microfluidic mixers 90–93. The device 60 is constructed from five device layers 61–65, including stencil layers 62–64 that have channels 74–77, 81, 83 and through holes 78–80, 82 cut through them. The stencils 62–64 are constructed from layers of single sided tape (three mil polypropylene carrier with water based adhesive on one side) and the channels are all forty-five mils wide except at overlap region 95. The bottom layer 65 is a 0.25 inch thick block of acrylic. Inlet ports 66–69 and outlet ports 70–73 are defined in the upper most device layer 61. All of the holes 66–69, 70–73 are 60 mils in diameter. The stencils 62–64 are adhered together between the outer device layers 61, 65 to form the completed device 60, shown in FIG. 3B.

In the prior art, microfluidic devices are constructed in a two-dimensional fashion, as approximated by the upper three mixers 91–93 of FIG. 3B. If two different fluids are injected into the two inlet ports 66, 67 of mixer 93, the fluids travel down their independent channel sections and meet at the central section of channel 74. In the central region, all of the flow is laminar. The fluids travel down their respective sides of the central section and fork until they reach the outlet ports 70, 71. Surprisingly, the fluid that entered into inlet port 66 exits almost completely out of channel 74 at exit port 70. The fluid that entered inlet port 67 exits out of exit port 71 almost exclusively. The only mixing that occurred in the central section of channel 74 is through diffusional mixing at the relatively small lateral interface of the liquids. Because the width of these channels (about sixty mils) is much greater than their height (about four mils), the interfacial contact area between the two fluids is very small and the molecules at the interface must diffuse up to thirty mils in order for complete mixing to occur. At room temperature, diffusional motion is not sufficiently rapid for this mixing to occur.

The prior art-type microfluidic mixers can be improved slightly by making the central channel longer and thereby extending the interfacial contact area between the two fluids as in mixers 91 and 92. In these mixers, the length of the mixing regions are extended. However, very little mixing occurs even in these mixers. In addition, a slower flow-rate allows more time for the diffusion process to occur. However, this also results in incomplete mixing over any reasonable time period.

Alternatively, an embodiment 90 of a microfluidic mixer according to the present invention is shown. In this mixer 90, the inlet channels 77, 83 were constructed on different layers 62, 64 of a three dimensional structure. The inlet channels 77, 83 are in fluid communication at overlap region 95 where the two fluids to be mixed are forced to enter into an outlet channel 81, in this case located on a layer 63 intermediate to the layers 62, 64 defining the two inlet channels 77, 83. In this embodiment, at the overlap region 95 the interfacial contact area between the two fluids extends all the way across the width of the channel 81 and is fifteen times greater than in the previous mixer 91. In addition, the average distance that the molecules need to diffuse in order for mixing to occur is now two mils, rather than thirty mils as in the previous mixers 91–93.

This mixing behavior was demonstrated by performing a simple acid-base reaction within the mixers. In the mixer 90, a 0.1M NaOH solution was injected into one inlet port 68, and a 0.5M HCl solution injected into the other inlet port 69. The NaOH solution contained a small amount of bromophenol blue indicator (which is purple in basic solution, and yellow in acidic solution). Upon entering the mixing area 95 of the mixer 90, the clear HCl solution and dark-purple NaOH solution mixed and reacted completely as evidenced by the color change of the indicator to a deep golden color (i.e., the stronger acidic solution neutralized the weaker basic solution, and the resulting mixture was weakly acidic). The reaction was also performed with a 0.1M HCl solution mixing with a 0.2M NaOH solution, in which the indicator was first dissolved in the acidic solution. In this experiment, the clear NaOH solution and yellow HCl solution mixed to create a dark purple fluid (in this case, the weaker acid is neutralized by the stronger base, resulting in a mixture that is weakly basic). In comparison, a mixer 93 according to a prior art design was also tested using these same solutions. In this mixer 93, little or no mixing occurred at the Interface of the two liquids. The solutions that came out of the outlets 70, 71 on either side were the same color and pH as the solutions that were inputted at the corresponding inlet side.

The two fluids were then injected into the microfluidic mixer 90 according to the present invention. Again, a clear NaOH solution was supplied to inlet port 69 and a yellow HCl solution (containing indicator) at inlet port 68. The two fluids begin to mix at the overlap region 95 and the mixing is nearly complete just after this region 95 within the outlet channel 81. Dark fluid color was observed within the outlet channel 81 and at the outlet ports 72, 73, which was indicative of the acid-base reaction going to completion.

Figure 4A:
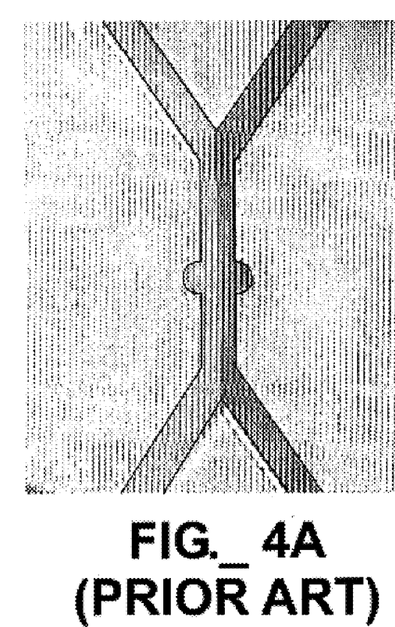
FIG. 4A is a top view photograph of a microfluidic mixing device with traced channel borderlines according to a first prior art design that promotes interfacial contact between two side-by-side fluids in a straight channel, wherein only minimal mixing occurs between the two fluids before the aggregate is split into two separate streams.
Figure 4B:
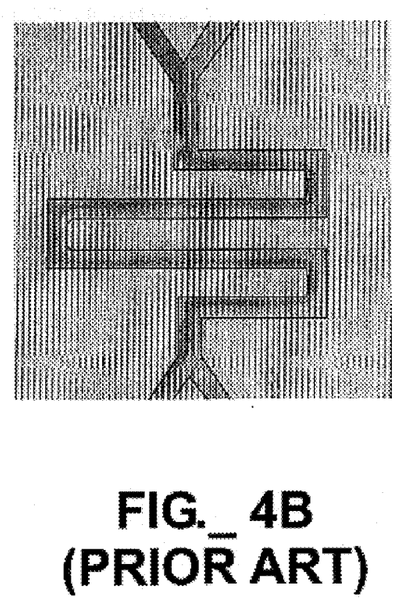
FIG. 4B is a top view photograph of a microfluidic mixing device with traced channel borderlines according to a second prior art design that promotes interfacial contact between two side-by-side fluids in a channel with several turns, wherein incomplete mixing occurs between the two fluids before the aggregate is split into two separate streams.
Figure 4C:
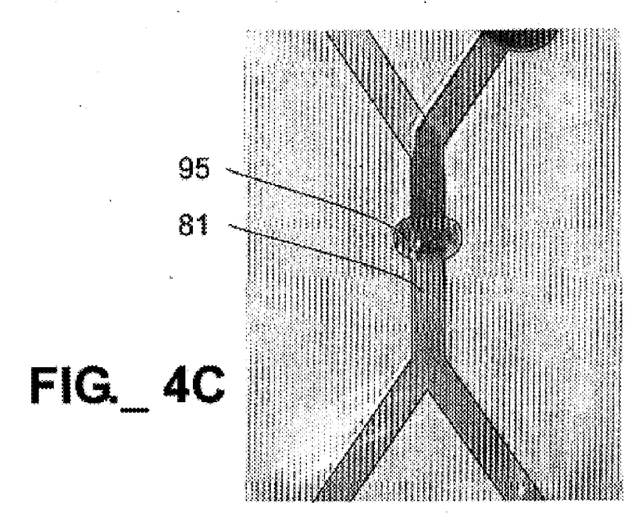
FIG. 4C is a top view photograph of a microfluidic mixing device with traced channel borderlines according to the present invention, demonstrating rapid and complete mixing between two fluids before the aggregate is split into separate streams.

The difference in mixing behavior was also demonstrated by injecting water that had been dyed yellow into inlet port 67 and blue-dyed fluid into inlet port 66. As the fluid flowed down the prior art-type microfluidic channels, no mixing occurred. Referring to FIG. 4A, depicting a prior art-type mixer 93, yellow fluid is injected into inlet port 67 and blue fluid into inlet port 66. Note that no mixing occurs in the length of the channel 74. Referring to FIG. 4B, depicting another prior art-type mixer 91, yellow fluid and blue fluid were injected into a snaking channel 76; still no mixing occurred. Finally, referring to FIG. 4C, the colored fluids were injected into the microfluidic mixer 90 according to the invention described herein. The two fluids begin to mix at the overlap region 95 and the mixing is complete just after this region 95 in outlet channel 81 and all of the fluid is green.

Figure 5A:
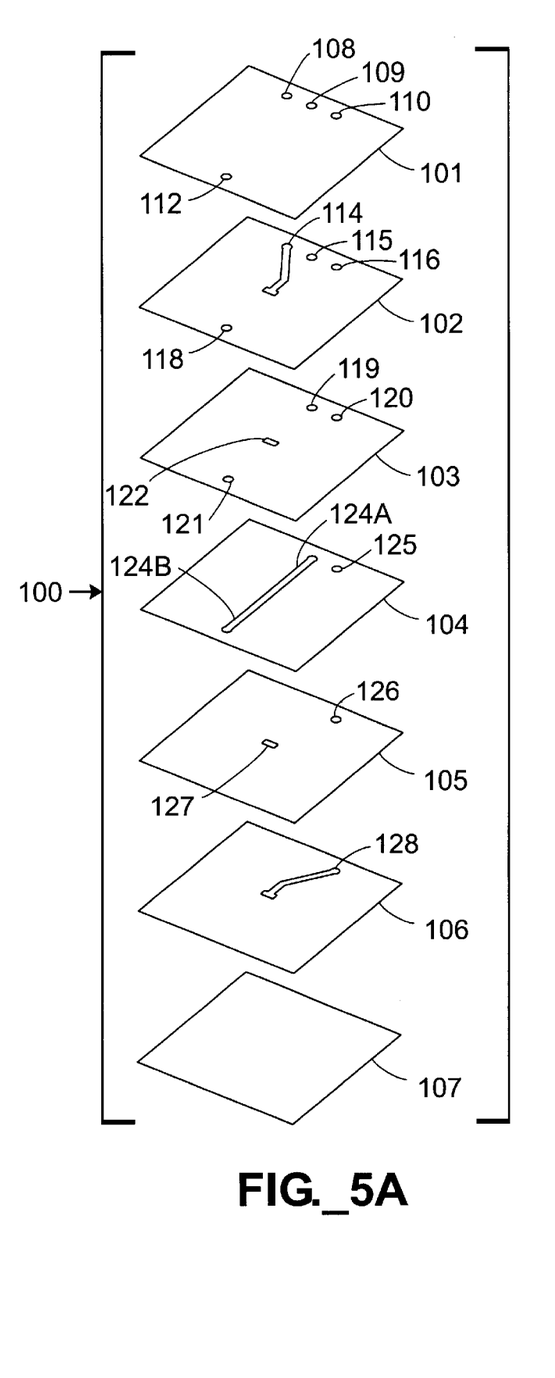
FIG. 5A is an exploded perspective view of a seven-layer microfluidic device capable of mixing three fluids.
Figure 5B:
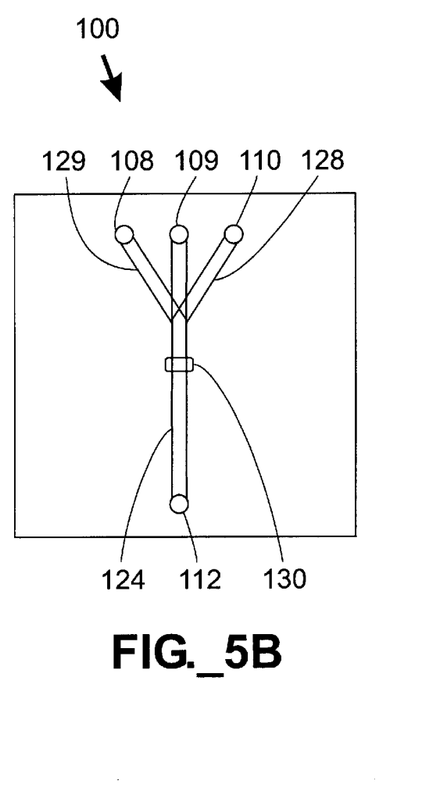
FIG. 5B is a top view of the assembled device of FIG. 5A.

More than two fluids can also be mixed with devices according to the present invention. Referring to FIGS. 5A–5B, a microfluidic mixing device 100 that receives and mixes three different fluids is shown. FIG. 5A shows seven device layers 101–107, including stencil layers 102,104,106, that define channels 114,124,128; through regions 122,127; and through holes 115, 116,118–121,125–126. Channel 124 includes an inlet portion 124A and outlet portion 124B. All of the channels 114,124,128 are sixty mils wide and the through holes are all eighty mils in diameter. The six uppermost device layers 101–106 are all constructed from single sided tape (three mil thick polypropylene backing with water based adhesive). The bottom layer 107 is a 0.25 inch thick block of acrylic. The top layer 101 defines inlet ports 108–110 and an exit port 112 in it. The assembled device 100 is shown in FIG. 5B.

In use, three different fluids are injected at the inlet ports 108–110. The three fluids each travel down their respective inlet channels 114,124A, 128 and meet at the junction point 130 by way of apertures 122,127. Immediately downstream of the junction 130, the fluid from inlet channel 114 is forced into the upper third of outlet channel region 124B, the fluid from inlet channel 124A occupies the middle third of outlet channel region 124B, and the fluid from inlet channel 128 occupies the bottom third of outlet channel region 124B. Again, the interfacial contact area is maximized in the outlet channel area 124B between the upper fluid and the middle fluid, and between the middle fluid and the lower fluid, thus causing very rapid diffusional mixing, so that the fluid that exits port 112 is fully mixed. This device 100 also allows for a tremendous range in mixing ratios. The flow rates of each of the fluids can be adjusted to allow a greater or lesser amount of each fluid to be added to the mixture.

Figure 6A:
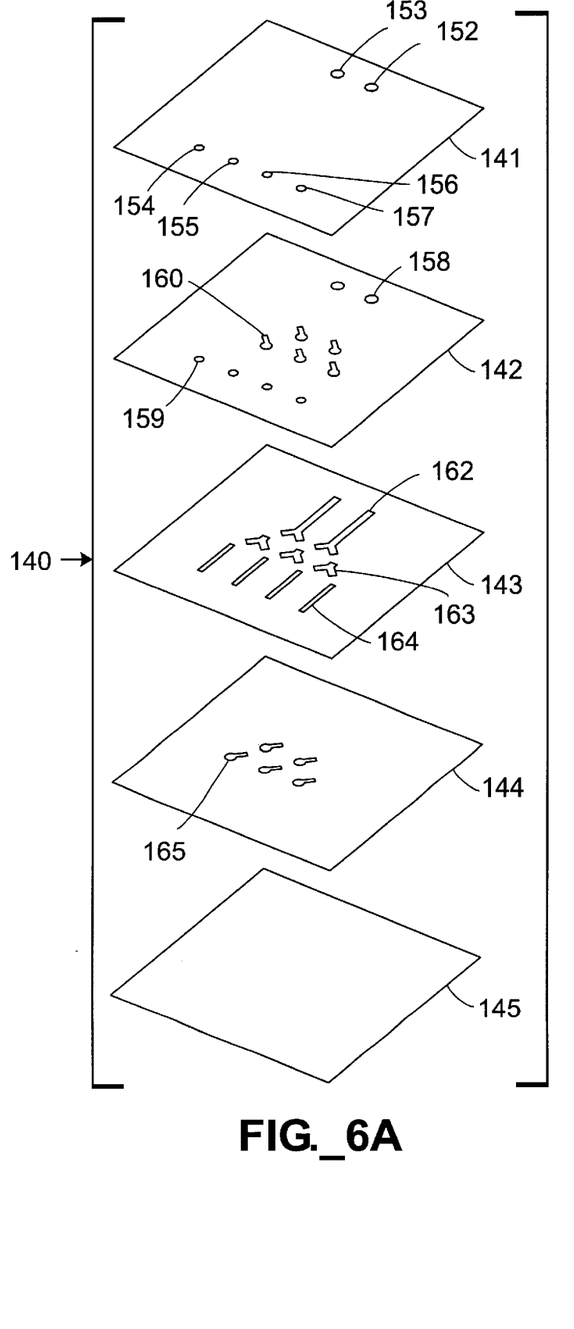
FIG. 6A is an exploded perspective view of a five-layer microfluidic mixing device capable of simultaneously mixing two fluid input streams in different proportions to yield four output streams.
Figure 6B:
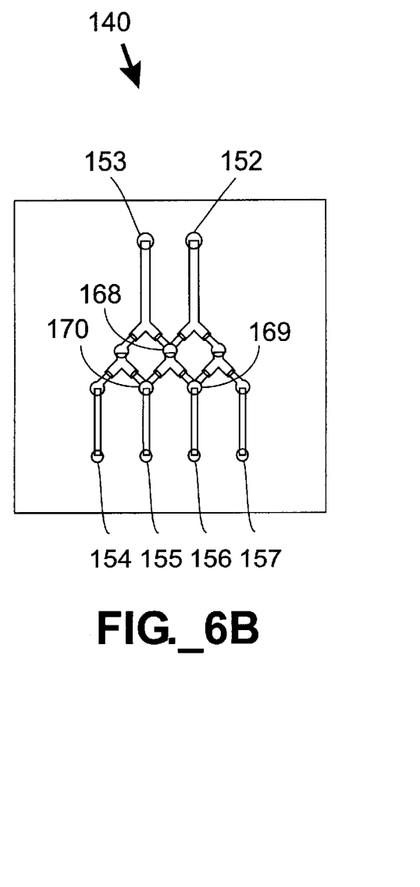
FIG. 6B is a top view of the assembled device of FIG. 6A.

A combinatorial microfluidic mixer 140 is shown in FIGS. 6A–6B. This device 140 brings in two different fluids and mixes them in four different stoichiometries.

Referring to FIG. 6A, a combinatorial microfluidic mixing device 140 is constructed from five device layers 141–145, including stencil layers 142–144, that define channels 160,162–165 and through-holes 158,159. Inlet ports 152,153 and outlet ports 154–157 are defined in the top layer 141. Channels 162,163, are forty-five mils wide, channels 160, 164,165 are thirty mils wide, and the overlap regions are fifteen mils in length. All of the round areas and holes are seventy mils in diameter. The uppermost four layers 141–144 are all constructed from single sided tape (3 mil thick polypropylene backing with water based adhesive). The bottom layer 145 is a 0.25 inch thick block of acrylic. In use, fluid A is injected at port 152 and fluid B at port 153. The fluids are split in the division sections of channel 162. At the microfluidic mixer region 168 fluids A and B mix to form A+B. The fluids move on to the splitter channels 163 to the next set of microfluidic mixer regions. At region 169, the mixture of A+B meets with pure A. The output is 3A+B.

At region 170, A+B meets with pure B, outputting 3B+A. The outputs of the combinatorial microfluidic mixer are as follows: 154 is pure B, 155 is 3B+A, 156 is 3A+B, 157 is pure A. Other combinations can be constructed. In practice the amounts of fluid mixing at each of the output is dependent on a number of factors, including flow rate, fluid properties and device geometry and chemistry.

The invention described and claimed herein is not to be limited in scope by the specific embodiments herein disclosed, since these embodiments are intended merely to illustrate certain aspects of the invention. All equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

What is claimed is:

1. A microfluidic separator comprising:
    a first stencil layer having a characteristic thickness;
    a single substantially linear inlet channel defined through the entire thickness of the first stencil layer;
    a second stencil layer having a characteristic thickness;
    a first outlet channel defined through the entire thickness of the second stencil layer;
    a third stencil layer having a characteristic thickness;
    a second outlet channel defined through the entire thickness of the third stencil layer; and
    a single overlap region permitting fluid to be communicated from the inlet channel to both the first outlet channel and the second outlet channel;
    wherein the first stencil layer is disposed between second stencil layer and the third stencil layer;
    wherein the inlet channel, first outlet channel, and second outlet channel are each adapted to maintain substantially laminar flow therein.

2. The microfluidic separator of claim 1 wherein the first stencil layer, the second stencil layer, and the third stencil layer are composed of substantially the same material.

3. The microfluidic separator of claim 1 wherein the second stencil layer defines a first surface bounding the inlet channel, and the third stencil layer defines a second surface bounding the inlet channel.

4. The microfluidic separator of claim 3 wherein the second stencil layer is composed of a hydrophobic material and the third stencil layer is composed of a hydrophilic material.

5. The microfluidic separator of claim 1 wherein each of the first stencil layer, the second stencil layer, and the third stencil layer have a thickness between about one micron and about five hundred microns.

6. The microfluidic separator of claim 1 wherein the first stencil layer, the second stencil layer, and the third stencil layer each have a thickness between about ten microns and about one hundred microns.

7. The microfluidic separator of claim 1 wherein the first stencil layer, the second stencil layer, and the third stencil layer each are fabricated with polymeric materials.

8. The microfluidic separator of claim 1 wherein at least one of the first stencil layer, the second stencil layer, and the third stencil layer is fabricated with self-adhesive tape.

9. The microfluidic separator of claim 1 wherein when combination of a first fluid and a second fluid are provided to the inlet channel, substantially all of the first fluid is provided to the first outlet channel and substantially all of the second fluid is provided to the second outlet channel.

10. The microfluidic separator of claim 9 wherein the first fluid is in gas phase and the second fluid is in liquid phase.

11. The microfluidic separator of claim 9 wherein the first fluid and the second fluid are substantially immiscible.

12. A microfluidic separator comprising:
    a first device layer having a characteristic thickness, a top surface, and a bottom surface;
    a single substantially linear inlet channel defined through the entire thickness of the first device layer and terminating in a single overlap region;
    a second device layer having a characteristic thickness and being disposed above the top surface;
    a first outlet channel defined through the entire thickness of the second device layer, the first outlet channel being in fluid communication with the overlap region;
    a third device layer having a characteristic thickness and being disposed below the bottom surface; and
    a second outlet channel defined through the entire thickness of the third device layer, the second outlet channel being in fluid communication with the overlap region;
    wherein the inlet channel, first outlet channel, and second outlet channel are each adapted to maintain substantially laminar flow therein.

13. The microfluidic separator of claim 12 wherein the first device layer, the second device layer, and the third device layer are composed of substantially the same material.

14. The microfluidic separator of claim 12 wherein the second device layer defines a first surface bounding the inlet channel, and the third device layer defines a second surface bounding the inlet channel.

15. The microfluidic separator of claim 14 wherein the second device layer comprises a hydrophobic material and the third device layer comprises a hydrophilic material.

16. The microfluidic separator of claim 14 wherein the second device layer comprises a hydrophilic material and the third device layer comprises a hydrophobic material.

17. The microfluidic separator of claim 12 wherein the first device layer, the second device layer, and the third device layer each have a thickness between about one micron and about five hundred microns.

18. The microfluidic separator of claim 12 wherein the first device layer, the second device layer, and the third device layer each have a thickness between about ten microns and about one hundred microns.

19. The microfluidic separator of claim 12 wherein each of the first device layer, the second device layer, and the third device layer are fabricated with polymeric materials.

20. The microfluidic separator of claim 12 wherein at least one of the first device layer, the second device layer, and the third device layer is fabricated with self-adhesive tape.

21. The microfluidic separator of claim 12 wherein when combination of a first fluid and a second fluid are provided to the inlet channel, substantially all of the first fluid is provided to the first outlet channel and substantially all of the second fluid is provided to the second outlet channel.

22. The microfluidic separator of claim 21 wherein the first fluid is in gas phase and the second fluid is in liquid phase.

23. The microfluidic separator of claim 21 wherein the first fluid and the second fluid are substantially immiscible.

* * * * *